(12) United States Patent
Bensoussan

(10) Patent No.: US 8,745,793 B2
(45) Date of Patent: *Jun. 10, 2014

(54) MEDICAL MATTRESS AND MATTRESS COVER

(75) Inventor: Jose Bensoussan, Los Angeles, CA (US)

(73) Assignee: Ubimed, Inc., Culver City, CA (US)

(*) Notice: Subject to any disclaimer, the term of this patent is extended or adjusted under 35 U.S.C. 154(b) by 162 days.

This patent is subject to a terminal disclaimer.

(21) Appl. No.: 12/790,538

(22) Filed: May 28, 2010

(65) Prior Publication Data
US 2010/0235992 A1     Sep. 23, 2010

Related U.S. Application Data

(63) Continuation-in-part of application No. 12/079,692, filed on Mar. 28, 2008, now Pat. No. 7,752,691.

(60) Provisional application No. 61/301,880, filed on Feb. 5, 2010.

(51) Int. Cl.
A47D 13/00     (2006.01)

(52) U.S. Cl.
USPC ........... 5/655; 5/724; 5/726; 5/652.1; 5/652.2

(58) Field of Classification Search
USPC ............ 5/603, 638, 643, 93.1, 120, 122, 127, 5/724–726, 737, 738, 655, 496, 653, 5/652.1–652.2
See application file for complete search history.

(56) References Cited

U.S. PATENT DOCUMENTS

| | | | | |
|---|---|---|---|---|
| 2,493,067 A | * | 1/1950 | Goldsmith | 5/726 |
| 2,495,482 A | * | 1/1950 | Rogatz | 297/467 |
| 2,959,794 A | * | 11/1960 | Souleles | 5/725 |
| 3,315,282 A | * | 4/1967 | Lowery et al. | 5/638 |
| 4,488,323 A | * | 12/1984 | Colburn | 5/692 |
| 4,862,535 A | * | 9/1989 | Roberts | 5/655 |
| 5,095,569 A | * | 3/1992 | Glenn | 5/490 |
| 5,214,087 A |   | 5/1993 | Braden et al. | |
| 5,317,767 A | * | 6/1994 | Hargest et al. | 5/725 |
| 5,361,430 A | * | 11/1994 | Wise | 4/572.1 |
| 5,423,099 A | * | 6/1995 | Gulli | 5/638 |
| 5,439,008 A | * | 8/1995 | Bowman | 128/875 |
| 5,561,876 A |   | 10/1996 | Petruzella | |

(Continued)

OTHER PUBLICATIONS

US Office Action issued for U.S. Appl. No. 12/079,692 on Mar. 3, 2009.

(Continued)

*Primary Examiner* — Nicholas Polito

(74) *Attorney, Agent, or Firm* — Intellectual Property Law Offices of Joel Voelzke, APC

(57) ABSTRACT

A mattress system includes a core mattress and a mattress cover. The core is made from a resilient material with a top surface that may be inclined with respect to the bottom surface. The removable mattress sheet covers the core and includes a breathable material that forms a hammock over a depression in the top surface. The subject rests at least partially on the hammock. One or more sidewalls of the mattress depression may have one or more openings to facilitate air circulation within the depression. The external ends of the openings may connect to an air or aerosol source to inject air or aerosols into the depression cavity. The core may be coated with a fire retardant, impermeable water-proofing or gas impermeable layer. A ventilator may be adapted within the mattress.

20 Claims, 19 Drawing Sheets

(56) References Cited

U.S. PATENT DOCUMENTS

| | | | | |
|---|---|---|---|---|
| 5,561,879 A | * | 10/1996 | Everall | 5/655 |
| 5,675,853 A | * | 10/1997 | Linge | 5/655 |
| 5,687,436 A | * | 11/1997 | Denton | 5/653 |
| 5,697,113 A | | 12/1997 | Shatz et al. | |
| 5,887,304 A | * | 3/1999 | von der Heyde | 5/726 |
| 6,052,849 A | * | 4/2000 | Dixon et al. | 5/643 |
| 6,112,343 A | * | 9/2000 | Dixon | 4/572.1 |
| 6,230,350 B1 | * | 5/2001 | Goldstein | 5/638 |
| 6,425,152 B1 | | 7/2002 | Quarles | |
| 6,460,207 B1 | | 10/2002 | Papay et al. | |
| 7,076,822 B2 | * | 7/2006 | Pearce | 5/655.5 |
| 7,234,181 B1 | | 6/2007 | Griggs | |
| RE40,754 E | * | 6/2009 | Morton | 5/655 |
| 7,752,691 B2 | * | 7/2010 | Bensoussan | 5/655 |
| 8,065,767 B2 | * | 11/2011 | Gabbai et al. | 5/655 |
| 2006/0162088 A1 | | 7/2006 | Daly | |
| 2006/0179568 A1 | | 8/2006 | Campbell | |
| 2006/0218726 A1 | | 10/2006 | Waters et al. | |
| 2007/0283502 A1 | | 12/2007 | Tullous | |
| 2007/0294831 A1 | * | 12/2007 | Siekman et al. | 5/653 |

OTHER PUBLICATIONS

US Office Action issued for U.S. Appl. No. 12/079,692 on Jun. 26, 2009.

US Office Action issued for U.S. Appl. No. 12/079,692 on Nov. 27, 2009.

International Search Report issued for PCT/US09/37222 on May 26, 2009.

* cited by examiner

60

130

140

MEDICAL MATTRESS AND MATTRESS COVER

CROSS-REFERENCE TO RELATED APPLICATIONS

This application is a continuation-in-part of U.S. application Ser. No. 12/079,692, filed on Mar. 28, 2008. This application also claims the benefit of U.S. Provisional Application 61/301,880, filed on Feb. 5, 2010. The teachings of both of these applications are incorporated herein by reference in their entireties.

FIELD OF THE INVENTION

The present invention relates generally to a mattress and mattress cover. More particularly, various embodiments disclose a mattress and mattress cover that are designed to help prevent Sudden Infant Death Syndrome (SIDS), and to help reduce the risk of plagiocephaly. In various embodiments the mattress cover also supports many other medical applications when free air flow is desired around a subject, for example for skin diseases or burn patients.

BACKGROUND OF THE INVENTION

Sudden Infant Death Syndrome (SIDS) is a significant cause of death among infants in their first year of life. To date, the underlying causes remain unexplained. The most recent research has shown, however, a connection between SIDS and blockage of the upper respiratory system. Consequently, many medical authorities today recommend that infants be placed on their backs with their spines straight (the so-called straight head position, or SHP). SHP ensures that the upper respiratory system is maximally opened. This reclined position reduces the possibility of re-breathing exhaled air. Physicians further recommend that infants be positioned such that their torsos are slightly elevated to reduce the risk of gastro-esophageal reflux. Overheating is also a factor known to increase the risk of SIDS. Suffocation is a well-known cause of infant death, particularly when the baby is placed or turns on its tummy in bed.

Because SIDS presents such a serious threat to infants, there is an immediate need for infant mattress that assists in the positioning of an infant so as to conform with current best practices for reducing SIDS.

Additionally, it has been noted that some infants develop a flat area on the skull (known as Flat Head Syndrome or positional plagiocephaly) during their first few months from sleeping on their backs all the time on a flat, firm surface. Doctors have noticed a startling increase of cases of plagiocephaly in the past 15 years. The onset of the surge coincides directly with the 1992 introduction of the American Academy of Pediatric "Back to Sleep" campaign advocating infant back sleeping to prevent SIDS. As more parents adopted these recommendations, cases of plagiocephaly skyrocketed. It is therefore desirable to also provide a mattress that will help to prevent infant plagiocephaly.

Moreover, some patients, for example burn patients, also need to be surrounded by air; it is desirable to provide free airflow around their lesions allowing better oxygenation and improved cicatricial processes, lowering the risk of infection. A mattress with a removable and washable mattress cover allowing free airflow is a must for these types of patients.

SUMMARY

Various embodiments disclose a removable mattress-cover having a mesh fabric. The mattress cover includes a mesh fabric sized to at least partially accept the body of the subject, to cover at least a portion of a mattress depression. The mesh material forms a hammock that is suspended over the bottom surface of the depression, and at least a portion of the subject may be disposed on this hammock. The hammock shape may be circular, oval, square, rectangular, polygonal, triangular or any other suitable shape.

The mattress depression may be a hole in the core mattress. The shape of the hole may also be circular, oval, square, rectangular, polygonal, triangular or any other suitable shape. In preferred embodiments arced shapes, such as circular shapes or oval shapes, are employed to reduce mattress collapse under the weight of the subject.

In other embodiments the depression may be provided by wings or arms extending from the core mattress that form a U-shaped depression or hole.

The core mattress may be made at least partially of different materials, including polyurethane foam, polyethylene foam, Latex, coco fibers, whole, cotton, polyester, plastic, carbon, fiberglass, metal, or any other suitable material.

In some embodiments, the core mattress may include springs to provide the desired resiliency of the top surface of the mattress.

In some embodiments, a core mattress made of foam, latex, coco fibers, or other suitable materials may be reinforced with other materials, such as with pieces of plastic, wood, metal or any other suitable materials. In some embodiments the reinforcing elements or elements may be in the form of a tube or other suitable shape disposed internally within the core mattress; in other embodiments the reinforcing element(s) may be disposed outside the core mattress as an external frame, or within the depression of the core mattress to prevent the core mattress padding from collapsing under the weight of the subject.

In some embodiments, the core mattress is made of foam with different densities, or includes hollow channels.

In some embodiments, the core mattress may be made of two or more different materials, for example a polyethylene layer and polyurethane layer or polyurethane layer and a plastic layer (or case) in order to make the core mattress less deformable.

In some embodiments, the core mattress may be at least partially replaced by a frame made, for example, from metal, plastic, wood, fiberglass, carbon fibers, magnesium, or other suitable materials.

In another embodiment, tubes of a frame structure may be covered with foam, latex, coco fibers, wool, cotton, polyester or any other suitable padding material to ensure that contact by the subject is comfortable.

In some embodiments, the core mattress may be enclosed in a fire retardant fabric or fibers layer.

In some embodiments, the core mattress may be covered at least partially with a fire retardant fibers layer or fabric.

In preferred embodiments the removable mattress cover forms a bag structure into which a core mattress is disposed. In such embodiments the mattress cover may further comprise a closing mechanism to close an opening of the bag-shaped structure. In such embodiments, the mattress cover may include an anchoring system (ribbons, laces or other suitable anchoring dispositive) to secure the mattress cover to the crib or bed. The anchoring system may help preventing the mattress from collapsing under the weight of the subject lying on the hammock and also may prevent a baby from accidentally asphyxiating under the mattress core.

In various embodiments, the core mattress (or reinforcing structure) may include an anchoring system, such as ribbons, laces or other suitable anchoring devices, to secure the core mattress to a crib or bed. In some embodiments the mattress cover may include one or more openings to permit the anchoring system to pass through the mattress cover.

In various embodiments, a bag-shaped mattress cover includes a flap in the opening end that may be employed to tuck around the mattress core to secure the mattress cover within the bag-like cover.

In various other embodiments, the removable mattress cover including the above described mesh fabric, forming a hammock, is not bag-shaped but instead covers at least partially the mattress top surface covering the core mattress depression, and may also at least partially or completely cover the core mattress sides and bottom; the mattress cover may be firmly attached to the mattress top, sides or bottom by a zipper, laces, hook and loop fasteners, or any other suitable mechanism.

In various other embodiments, the removable mattress cover including the above described mesh fabric, forming a hammock, is designed as a fitted sheet covering the top, the sides and partially the bottom of the core mattress, and may include elastics sewn into the lowers corners, or any other suitable mechanism, to help keep the mattress cover in place over the core mattress.

In various embodiments, the removable mattress cover is entirely made of a mesh fabric.

In various embodiments, the removable mattress cover is made at least partially of a breathable fabric covering the core mattress depression.

In various embodiments at least one sidewall of the core mattress comprises an opening, depression, or elevated portion for providing air, oxygen or aerosols into the central depression or hole. An external end of the opening may be adapted to connect to a supply tube that supplies air, oxygen, aerosols or combinations thereof through the mesh fabric of the mattress cover.

In various embodiments at least one sidewall of the mattress-cover comprises an opening for providing air, oxygen or aerosols through a breathable fabric of the mattress cover. An external end of the opening may be adapted to connect to a supply tube that supplies air, oxygen, aerosols or combinations thereof through the breathable fabric.

In various embodiments the mattress cover sidewall opening(s) may be closed by a breathable fabric.

In various preferred embodiments the top surface of the mattress is inclined with respect to the bottom surface.

In various other embodiments the top surface is at least partially parallel to the bottom surface. The horizontal portion of the top surface may support the head allowing an opened superior airway and straight head position for better oxygenation even with an inclined trunk.

In various embodiments, the mattress core includes an electric ventilator.

In various embodiments, the electric ventilator is removably disposed in the core mattress depression or hole or in a ventilation channel or depression.

DETAILED DESCRIPTION

Figure 1A:
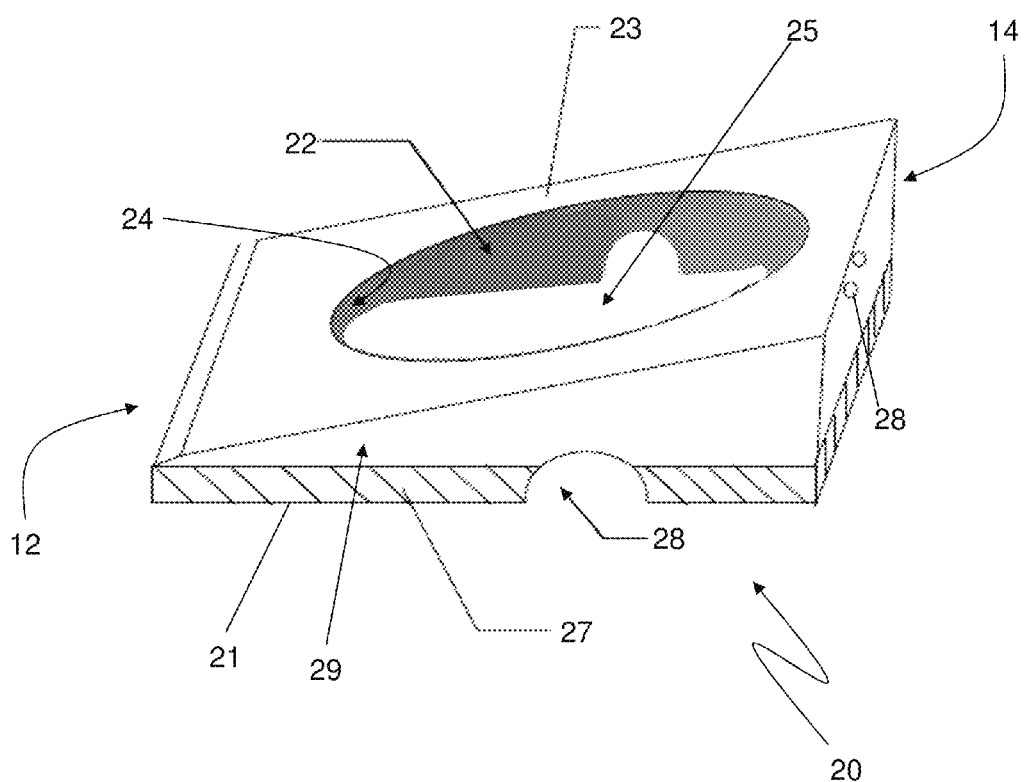
FIG. 1A is a perspective view of an embodiment core mattress.
Figure 1B:
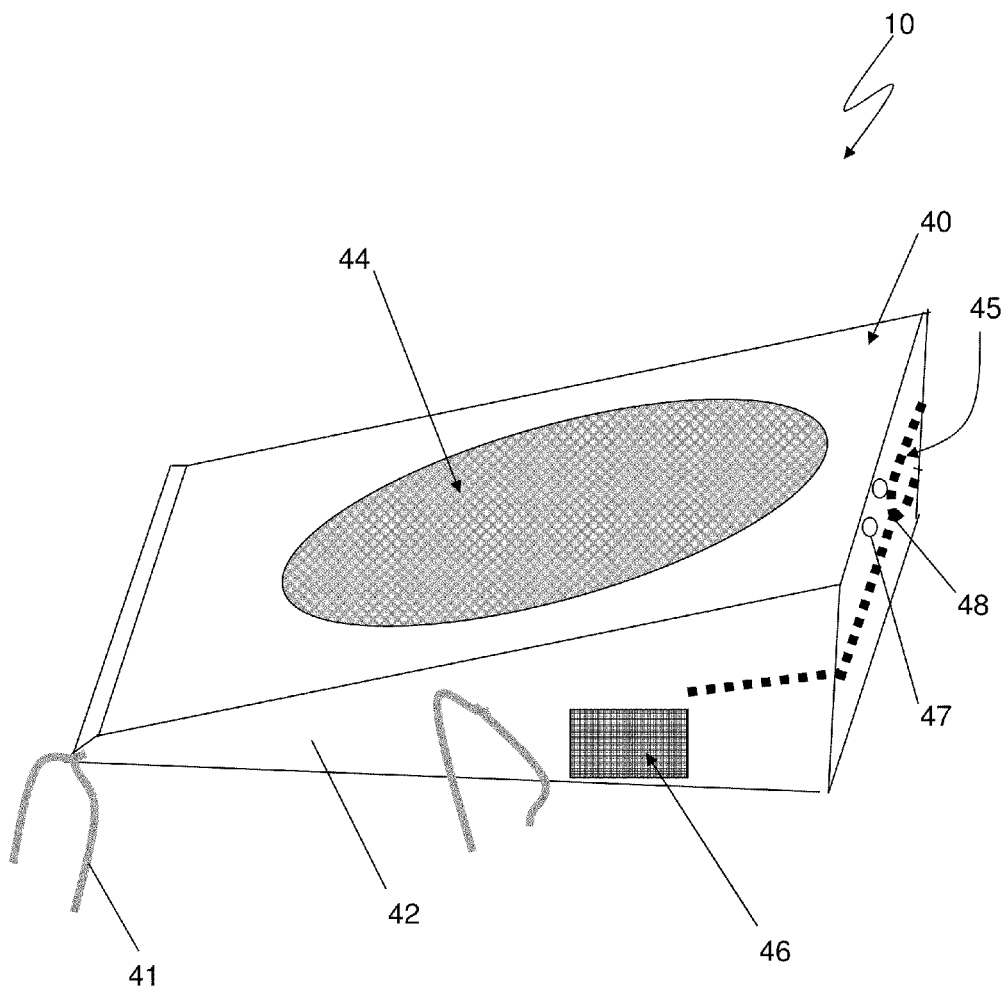
FIG. 1B is a perspective view of an embodiment mattress system.
Figure 1C:
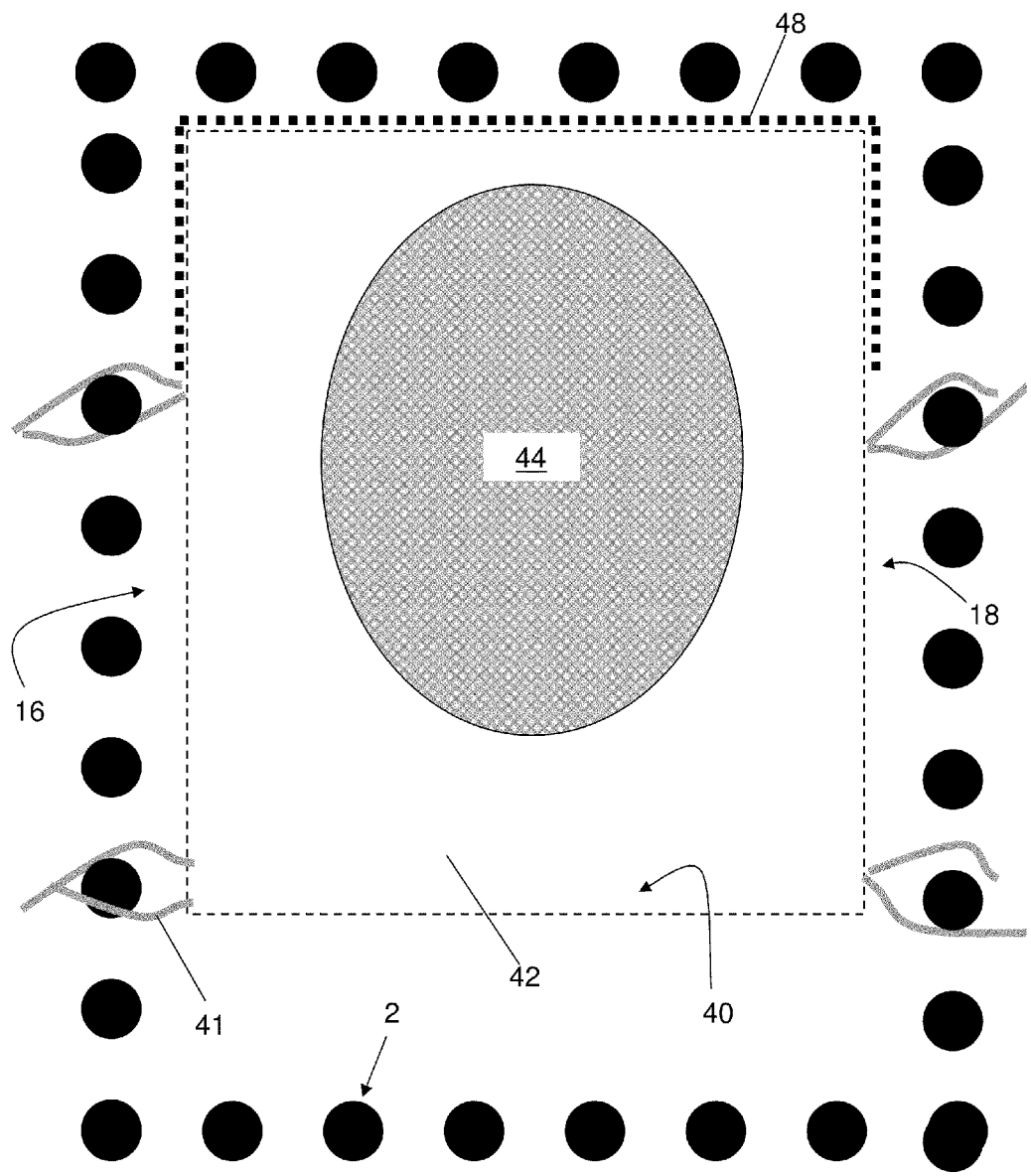
FIG. 1C is a top view of an embodiment mattress system coupling to an external device.
Figure 1D:
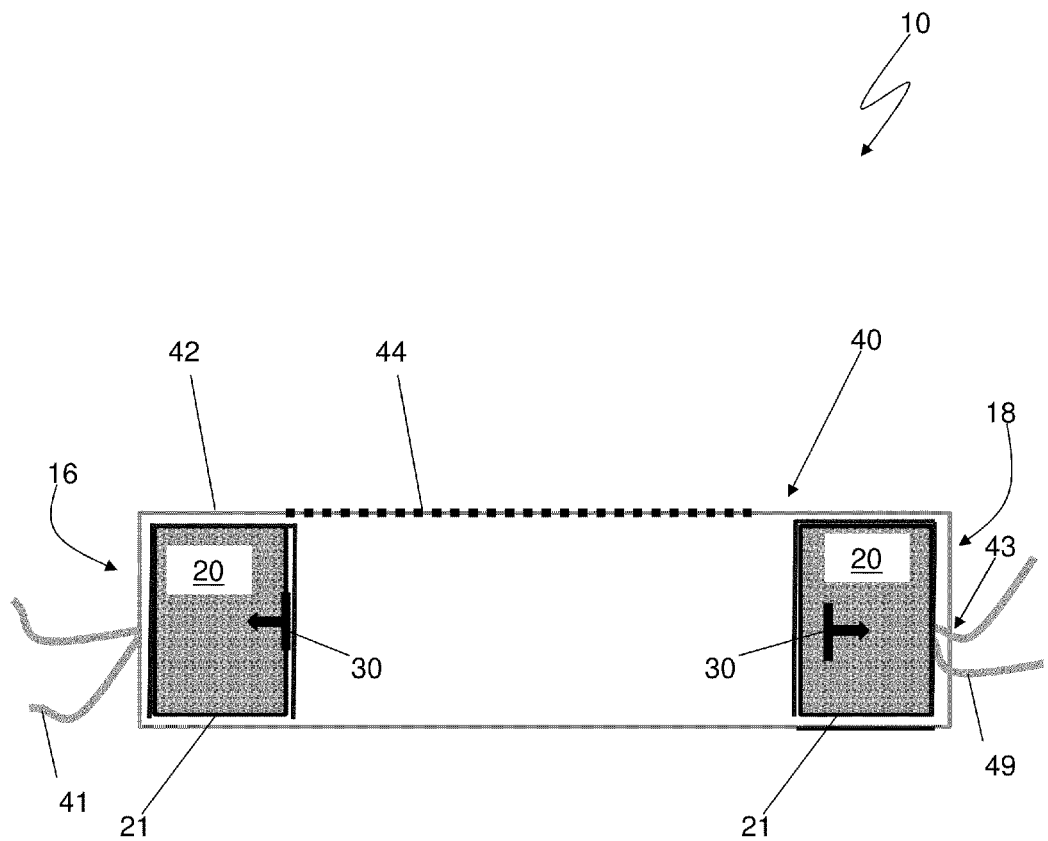
FIG. 1D is a cross-sectional view of an embodiment mattress system.
Figure 1E:
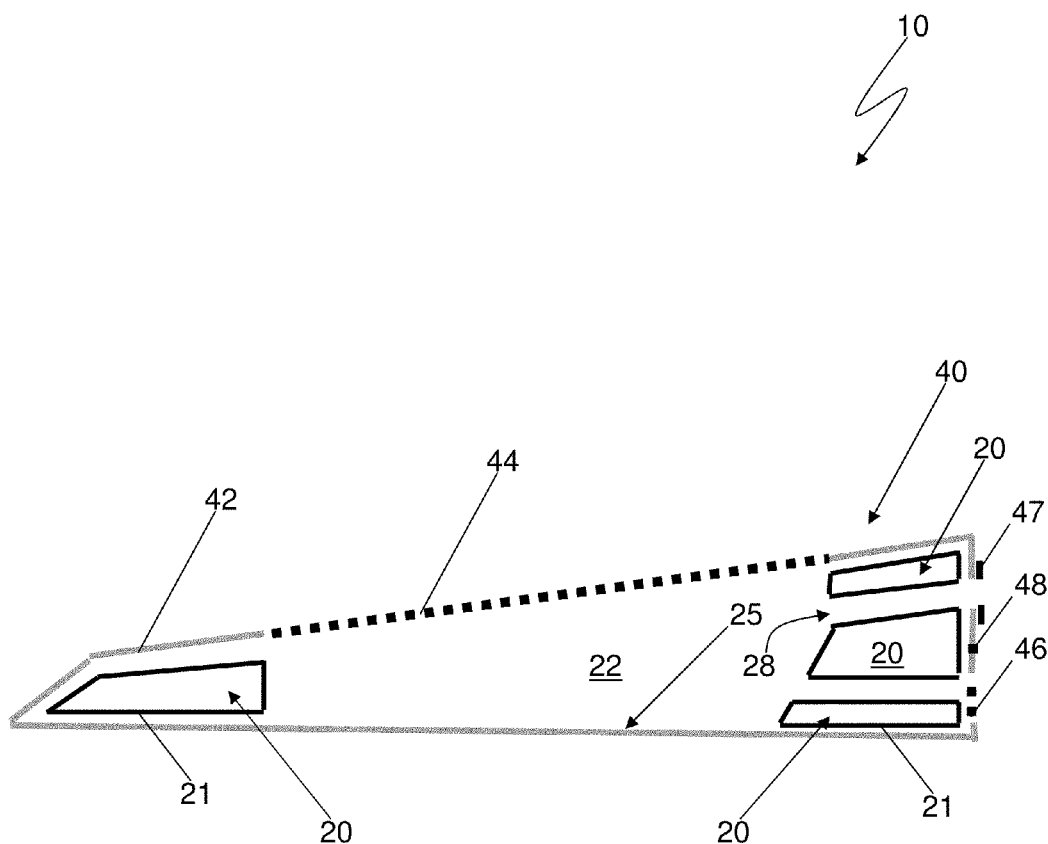
FIG. 1E is another cross-sectional view of an embodiment mattress system.

Reference is drawn to FIGS. 1A-1E, which disclose an embodiment mattress system 10 that includes a core mattress 20, with an optional stiffening system 30, and a mattress cover 40. Depending upon the intrinsic stiffness or rigidity of the core mattress 20, the core mattress 20 may be further reinforced with the stiffening system 30. The stiffening system 30 may prevent the core mattress 20 from bending when under the weight of a subject. In preferred embodiments the stiffening system 30, if present, is disposed within the core mattress 20. The stiffening system 30 may be made from any suitable material, such as plastic, wood or metal and may provide a tube-like or frame-like structure to reinforce the core mattress 20. In some embodiments the stiffening system 30 is made from a foam that is more rigid than the surrounding material of the core mattress 20; hence, the core mattress may comprise two or more different types of foam, a first that is more resilient and used for padding, and a second that is more rigid and serving as the stiffening system 30.

The core mattress 20 may be made from a resilient material, or from a plurality of different materials, such as polyurethane foam, polyethylene foam, Latex, coco fibers, whole, cotton, wool, polyester, plastic, carbon, fiberglass, metal, or any other suitable materials. For example, in certain embodiments the core mattress 20 is made from polyurethane foam. In other embodiments the core mattress 20 is made from a base of polyester foam on which is over-molded or glued a second layer made of polyurethane foam. In other embodiments the core mattress 20 is made from natural latex. Other suitable materials with requisite resilience and stiffness may be employed for the core mattress 20, either alone or in combination with the stiffening system 30. For example, the embodiment core mattress 20 has a base portion 27 that is made from polyethylene or plastic, and a top portion 29, affixed to the base portion 27, that is made from polyurethane. It will be appreciated, however, that other variations are possible. For example, the core mattress 20 may have a shell made from a resilient polymer, such as polyurethane, latex, or the like, that is filled with a ticking, such as wool, cotton or another type of polymer, such as foam.

The core mattress 20 has a bottom surface 21, which may serve as a base for the mattress system 10, and a top surface 23. The top surface 23 may be inclined with respect to the bottom surface 21, and hence the subject may lie at an inclined angle with respect to the base surface 21 so as to help prevent gastro-esophageal reflux. That is, the height of the core mattress 20 may increase from an anterior end 12 to a posterior end 14. The angle of inclination may be, for example, from 5 to 30 degrees, more preferably 20 to 30 degrees. The subject is aligned on the mattress 10 so that the feet are towards the anterior end 12 while the head points towards the higher posterior end 14. By way of a specific example adapted for babies or infants, the core mattress 20 may have a width from left side 16 to right side 18 of about 23 to 28 inches, and a length from anterior end 12 to posterior end 14 of about 36 to 39 inches. The anterior end 12 of the core mattress 20 may have a height of about 1 to 3 inches, while the posterior end 14 may have a height of 6 to 12 inches. Other embodiments that are adapted, for example, for adult patients, such as burn victims, may be scaled accordingly, and the stiffening system 30, if present, may be similarly adjusted accordingly.

It is preferred that at least the top surface 23 of core mattress 20 be moisture resistant, and preferably the entire core mattress 20 is moisture resistant. Any suitable means may be employed to make the core mattress 20 resistant or impermeable to moisture. For example, the external surfaces 21, 23 of the core mattress 20 can be enveloped in, or coated with, an impermeable plastic sheet, such as a vinyl laminate cover. Additionally, preferred embodiment core mattresses 20 are preferably fire retardant, or enclosed in fire retardant layers, such as aramid or para-aramid synthetic fibers. These fire retardant layers may be, for example, glued or sewn onto to the outside surface of the core mattress 20. In preferred embodiments the external surface of the core mattress is also water-proof and gas impermeable. Additionally, the external surface of the core mattress is preferably stain-resistant.

The top surface 23 of core mattress 20 includes a depression 22 for accepting the head and torso, for example, of the subject. For purposes of the following, it should be understood that the term "depression" is intended to include both indentations in the top surface 23, holes passing all the way through the core mattress 20, cut-out sections or regions of the core mattress 20, and combinations thereof. Although preferred embodiments have only a single depression, it will be appreciated that multiple depressions are also possible. Again, by way of an example mattress 20 for an infant or baby, the depression 22 may have a width of about 14 inches, and a length of about 17 inches; the posterior end 14 of depression 22 may be spaced about 4 inches from the posterior end 14 of core mattress 20. In preferred embodiments the depression 22 is arcuate in shape, such as circular, oval or the like, as such shapes may better resist deformation when the mattress system 10 is under the weight of a subject. Other shapes, however, are certainly possible, such as square, rectangular, polygonal, triangular or the like.

The anterior end 12 of depression 22 may optionally include a surface 24 that acts as a buttock stop for the subject. Because the subject may rest in an inclined position, the subject may have a tendency to slide towards anterior end 12. However, the subject may further rest partially disposed within depression 22. Hence, buttock stop 24 serves to support the buttocks of the subject to prevent any anterior sliding of the subject. Buttock stop 24 may have an angle of 20 to 30 degrees, for example, with respect to bottom surface 21. The lower legs and feet of the subject may thus rest on the anterior end 12 of the top surface 23, while the upper legs or buttocks of the subject rest against the buttock stop 24 and the remainder of the subject rests above the bottom surface 25 of depression 22, as discussed in more detail below.

In certain embodiments a removable tray, made, for example, of plastic, may be disposed within the depression 22 below the subject to catch fluids, such as regurgitations, from the subject supported above the depression 22. An absorbent material or the like may further line the tray. Alternatively, only the absorbent material may be used to collect moisture falling within depression 22.

For various embodiments, the posterior end 14 of depression may further include one or more openings 28 in the core mattress 20. It will be appreciated, of course, that the openings 28 may be placed anywhere within the sidewalls of the depression 22, however. For example, openings 28 on the left 16 and right 18 sidewalls of the mattress 20 may be provided that extend to the bottom surface 21. The openings 28, in communications with external (i.e., external to depression 22) air or air sources, may facilitate the circulation of air within the depression 22. Additionally, posterior or external end 14 of the one or more openings 28 may be adapted to receive a supply tube to provide oxygen or aerosols to the subject via the depression 22. In some embodiments, one or more of the openings are slits in the core mattress 20. As known, oxygen and aerosols may be distributed by wall tubes in a hospital, or by bottles or devices; one or more of the openings 28 may therefore have a connector adapted to removably connect with such supply sources. In this manner various embodiment mattresses 10 may accommodate respiratory diseases of the subject, if present, or facilitate the continuous and thorough oxygenation of the subject to facilitate, for example, cicatricial processes and prevent infection.

Mattress cover 40 covers the top surface 23 of the core mattress 20, and in some embodiments, as shown in FIG. 1, envelopes the entire core mattress 20. The mattress cover 40 is preferably fire retardant and stain-resistant. Some embodiments may optionally include one or more anchoring devices 41 at the anterior 12, posterior 14, left 16 or right 18 ends that provide an anchoring system used to secure the cover 40 to the core 20 or to an external device, such as crib. Any suitable anchoring devices may be employed, such as laces, snaps, hooks, hook and loop fastener, or the like. For example, as shown in FIG. 1C, the anchoring devices 41 may be attached to the outside surface of the core mattress 40 and used to mechanically couple to slats 2 of a crib. Hence, when placed under tension from a subject, the mattress cover 40 may transmit this tension to the slats 2 by way of the anchoring devices 41; the anchoring devices 41 may thus prevent the cover 40 from excessively deforming under the weight of the subject. Similarly, as shown in FIG. 1D, an embodiment core mattress 20 may include anchoring devices 49 to distribute the load of the subject on the core mattress 20 and thus prevent excessive deformation of the core mattress 20. The anchoring devices 49 provide an anchoring system that may be coupled to the external surface of the core mattress 20 and pass through openings 43 in the mattress cover 40 to attach to an external device, such as the slats 2 of a crib. The mattress cover 40 may thus include openings 43 that are in register with the corresponding anchoring devices 49 on the core mattress. The anchoring devices 41, 49 may also prevent the creation of a dangerous gap between the top of the mattress and the crib and thus prevent a baby from crawling under the mattress and suffocating.

In the preferred embodiments the mattress cover 40 has a bag-like shape that has an opening 45 can be closed with a closing mechanism 48, such as a zipper, buttons, hook and loop fastener or the like. In some embodiments the closing mechanism 48 may be a flap in the opening 45 that goes over or around the core mattress 20, in much the same manner as is used for pillow cases to retain a pillow. The shape of the mattress cover 40 is preferably tailored to the specific shape of the core mattress 20 to provide a snug fit of the cover 40 over the core 20. The preferred embodiment mattress cover 40 thus has a bottom surface, which may serve as a base for the mattress system 10, and a top surface. The top surface may be at least partially inclined with respect to the bottom surface, consistent with the inclination of the core mattress 20 over which the cover 40 is intended to snugly fit, and hence the subject may lie at an inclined angle with respect to the base surface so as to help prevent gastro-esophageal reflux.

In preferred embodiments, whatever the actual shape of the mattress cover, the mattress cover is preferably easily removable from the core mattress so as to facilitate cleaning of the mattress cover. Hence, the mattress cover is also preferably easily re-attachable to the core mattress to provide for re-use of the mattress cover after cleaning. For example, because of the closable opening 45, the cover 40 may be easily removed from the core 20 for cleaning. Specifically, the core mattress 20 may be removed through opening 45, the mattress cover 40 may then be washed, such as by placing it into a standard washing machine or the like, dried, and then reinstalled back over or around the core mattress 20 and the closing mechanism 48 closed to secure the cover 40 to the core mattress 20.

In preferred embodiments the mattress cover 40 is formed from two distinct types of fabric for corresponding regions of the core mattress 20. The cover 40 includes a mesh-like fabric 44 that is positioned so as to be disposed across the depression 22 when installed on the core mattress 20. The mesh-like fabric serves as a hammock upon which the subject lies, either completely or partially, supported and suspended above the bottom surface 25, and may be made, for example, from a soft material that is to directly contact the subject, such as cotton, polyester, nylon, coco fibers or linen. The hammock 44 may be, for example, substantially the same shape as the depression 22 over which it is installed. For purposes of the following, "mesh-like" means fabrics that have repeated holes or openings, such as meshes, nettings or the like. This mesh-like material 44 provides a highly breathable interface for the subject to ensure a maximum recirculation of oxygenated air around the subject, and further permits the easy draining away of liquids emanating from the subject. By way of example, the hammock fabric 44 for an infant may have a width of about 14 inches, and a length of about 20 inches; the posterior end 14 of the hammock fabric 44 may be spaced about 4 inches from the posterior end 14 of the mattress cover 40. In some embodiments, the hammock fabric 44 will accept the head and torso or the entire body of the subject.

For those portions of the fabric 44 that are in contact with the subject, the width of the spacings in the webbing that make up the mesh-like structure 44 is ideally less than the width of the fingers of the subject; for example, in preferred embodiments the mesh opening will not admit a 0.250 inch diameter rod with a full radius tip. In certain embodiments, the mesh-like fabric 44 may further include an underlying reinforcing mesh that does not directly contact the subject, which may be made from a stronger material, such as nylon. Hence, the mesh-like hammock 44 may be formed from two separate materials: a soft, upper material upon which the subject lies in direct contact, which has a relatively narrow webbing spacing (i.e., less than the width of the fingers of the subject), and an optional underlying reinforcing mesh that the subject does not directly contact that provides additional support for the hammock 44.

In certain embodiments, the sturdier reinforcing material for the hammock 44, if present, may be attached (for example, by way of a zipper, snaps, hook and loop materials or the like) to the mattress core 20 around the depression 22 to reinforce the upper surface of the hammock 44 provided by the topmost, softer mesh fabric 44. In yet other embodiments, the remainder of the cover 40 may also be further provided with an additional mesh-like fabric to provide reinforcement against the weight of the subject. The underlying reinforcing mesh may be removably attached to the core mattress 20 by any suitable attaching mechanism. Alternatively, the underlying reinforcing mesh may be attached to the mattress cover 40 itself. In certain embodiments the underlying reinforcing mesh also extends under the remainder portions 42 of the cover 40 that are external to the mattress depression 22 to provide reinforcement over the entirety of the cover 40 or over the top surface of the cover 40. All or the majority of the remainder 42 of the cover 40 may be made from another type of fabric, such as a standard cotton cloth, poly-cotton or the like, and corresponds to those regions of the core mattress 20 that are external to the depression 22 and are connected to the periphery of the hammock portion 44. In yet other embodiments, the hammock 44 may be made from a breathable fabric that is not a mesh-like material, such as knitted polyester or nylon.

The mesh-like portion 44 of the cover 40 permits fluids from the subject to easily fall onto bottom surface 25 of depression 20, such as into a catchment, without pooling on the cover 40. The breathable surface 44 also ensures that a maximum amount of airflow is available to the subject, which is particularly important if the subject has turned onto his or her stomach, helps to reduce SIDS and assists in the healing and infection prevention for burn victims and may be recommended for certain skin disease therapies. The curvature of the hammock 44 may also help to prevent plagiocephaly. Air flow from openings 28 helps to avoid the re-breathing of air. The openings 28 may also permit the administration of therapeutic amounts of oxygen or aerosols. The cover 40 may further combine additional sections of mesh-like or breathable materials 46 that are positioned so as to be in register with the openings 28 within the core mattress 20 to ensure the maximum circulation of air within the depression 22.

As known, oxygen and aerosols may be distributed by wall tubes in a hospital, or by bottles or devices; one or more of the openings 28 may therefore have a connector adapted to mate with such supply sources. Hence, one or more of the openings in the mattress cover 40 may be reinforced with a suitable connecting piece 47. For example, the cover 40 may further comprise an adaptor 47 sewn or otherwise directly connected to the cover 40 to mate with the air-supply hose and the opening 28. Alternatively, the cover 40 may simply have holes in register with the openings 28 instead of the breathable material 46. Variations of the two are also possible, with some openings being covered by the breathable material 46 and others exposed by corresponding holes in the cover 40. Additionally a ventilator, such as an electric ventilator, may be disposed in the mattress core 20 to help renew and circulate air within the depression 22 and increase the airflow through the hammock structure 44. The ventilator may, for example, be coupled to an opening 28 via an air hose, or may even be disposed with the opening 28 itself. In this manner various embodiment mattress sheets may accommodate respiratory diseases (or skin diseases) of the patient, if present.

The hammock portion 44, including any underlying supportive layer if present, is preferably tailored to conform with buttock stop 24 so that when the subject lies in the hammock provided by the breathable fabric 44, the buttocks of the subject rest comfortably against the stopping surface 24. The hammock 44 is preferably less deformable than the core mattress 20, and hence underlying supportive webbing may be desirable to reinforce the softer, upper webbing of the hammock 44 that contacts the subject. Alternatively, as discussed earlier, an anchoring system 41 may be provided to take up some of the strain imposed by the weight of the subject and distribute it to another mechanical element, such as a crib, bed frame or the like.

As noted above, in some embodiments the mattress system provides a sloped top surface that includes a hammock onto which the subject is placed and suspend over a depression. Because of the sloping nature of the top surface, the subject may tend to slide towards the posterior end of the mattress system. Hence, in some embodiments the mattress cover 40 may include a harness or the like which may be used to prevent sliding of the subject towards the posterior end of the core mattress. Any suitable harnessing system as known in the art, such as a conventional baby harness, may be employed.

As indicated, the core mattress 20 may deform under the weight of the subject. The depth of the hammock 44 (i.e., how far hammock 44 extends into depression 22) may thus be a function of the width of fabric forming the hammock 44, resiliency of the hammock fabric 44 (in combination with any underlying reinforcing mesh), the width of depression 22, and the resiliency of core mattress 20. Hence, in embodiments where the core mattress 20 readily deforms under the weight of a subject, it may be desirable to have the hammock portion 44 disposed relatively tightly over the depression 22 so that the final desired curvature of the hammock 44 is achieved under the weight of the subject. For example, the hammock 44 may initially be flat, but subsequently curve under the weight of the subject. Alternatively, by way of example the length of the anchoring system elements 41 may be designed so as to prevent extension of the hammock 44 into the depression 22 beyond a predetermined distance.

In some embodiments, the bottom surface 25 of core mattress within depression 22 may have a secretion trail for the removal of fluids; in such embodiments, a suitable slit or opening may be made in any of the sidewalls of depression 22 in the core mattress 20 to effect removal of such secretions.

The hammock 44 provided by the meshed or breathable fabric and underlying reinforcing mesh or breathable fabric (if present), in conjunction with the mattress depression 22, ensures that the subject is provided a maximal amount of clean, fresh air, which is believed to assist in preventing SIDS and to help treat various skin diseases, injuries or both. The conformal curvature of the hammock 44 with an infant's skull may also help to prevent plagiocephaly. The mattress system 10 ventilation allows air flow, which may lower sweating of the subject. Moreover, liquids, such as milk, urine, vomit or the like, will fall though the meshed fabric(s).

Figure 2:
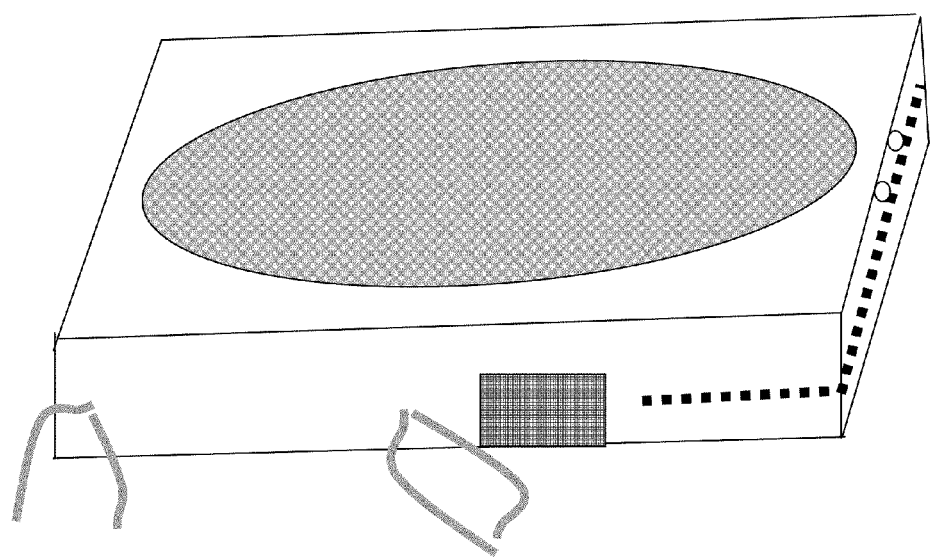
FIG. 2 is a perspective view of another embodiment mattress system.

The following discussed variations to the above-disclosed embodiment. As shown in FIG. 2, in some embodiments the top surface of the core mattress may be parallel to the bottom surface of the core mattress, and the mattress cover may be adapted accordingly so as to provide a snug fit around the core mattress.

Figure 3A:
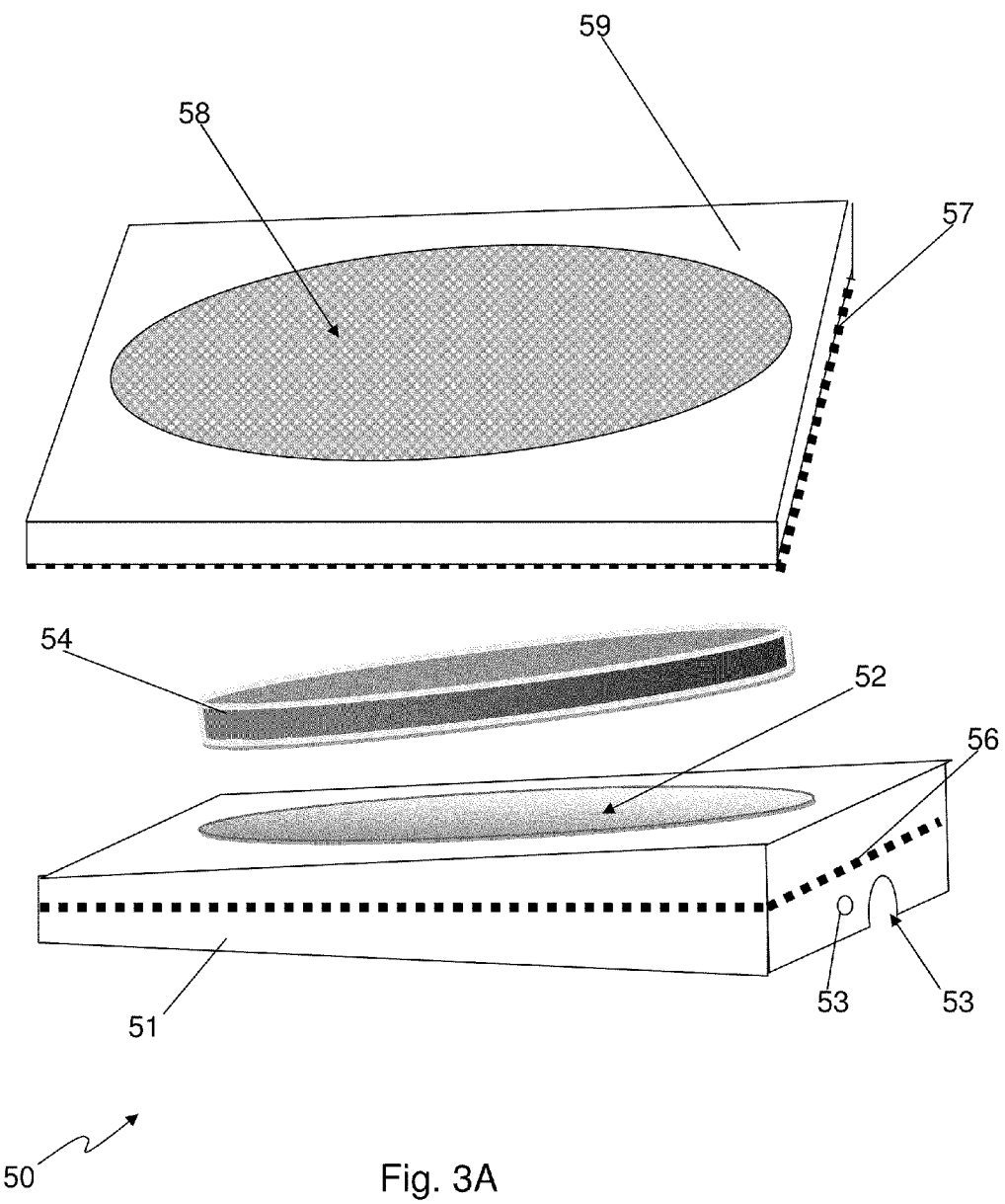
FIG. 3A is an exploded perspective view of yet another embodiment mattress system.
Figure 3B:
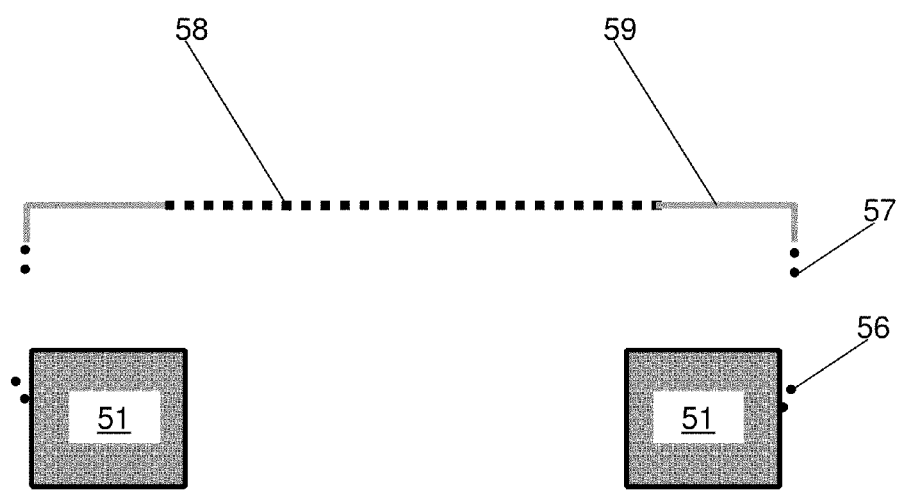
FIG. 3B is a cross-sectional view of the embodiment shown in FIG. 3A.

Preferred embodiments use a mattress cover that completely encloses the core mattress. However, this is not required. FIG. 3 is an exploded perspective view of another mattress system 50, which includes a core mattress 51 having a depression 52, a stiffening system 54 and a mattress cover 59. The mattress cover 59 includes a breathable, preferably mesh-like, hammock portion 58, which may be set within a second fabric, and an anchoring system 57 for coupling to the core mattress 51. The core mattress 51 also comprises a anchoring system 56 that is configured to couple with the mattress cover anchoring system 57. The anchoring systems 56, 57 may be zippers, hook and loop fasteners, snaps, hooks and holes, laces or the like. For example, hooks 56 inserted on the mattress 51 sides may receive corresponding holes 57 in the mattress cover 59; alternatively, for example, one half 56 of a zipper may be attached to the mattress core 51 and corresponds with the other half of the zipper 57 that is attached to the removable mattress cover 59. The depression 52 may be oval shaped and may receive around its periphery an ring-like, oval-shaped stiffening system 54 that prevents sagging or collapse of the sidewalls of the depression 52. The stiffening system 54 may be made from any suitable material to impart greater rigidity to the sidewalls of the depression 52. As in the previous embodiment, the core mattress 51 may include openings 53 to facilitate the recirculation of air within the depression 52.

In an alternative to the above embodiment system 50, the mattress cover may be designed as a fitted sheet that fully covers the top and sides of the core mattress, and extends partially to the underside of the core mattress. Such an embodiment mattress cover may include, for example, elastic materials sewn into the corners of the cover that serve as a anchoring system to elastically couple the mattress cover with the core mattress and hence remain in position over the core mattress.

Figure 4:
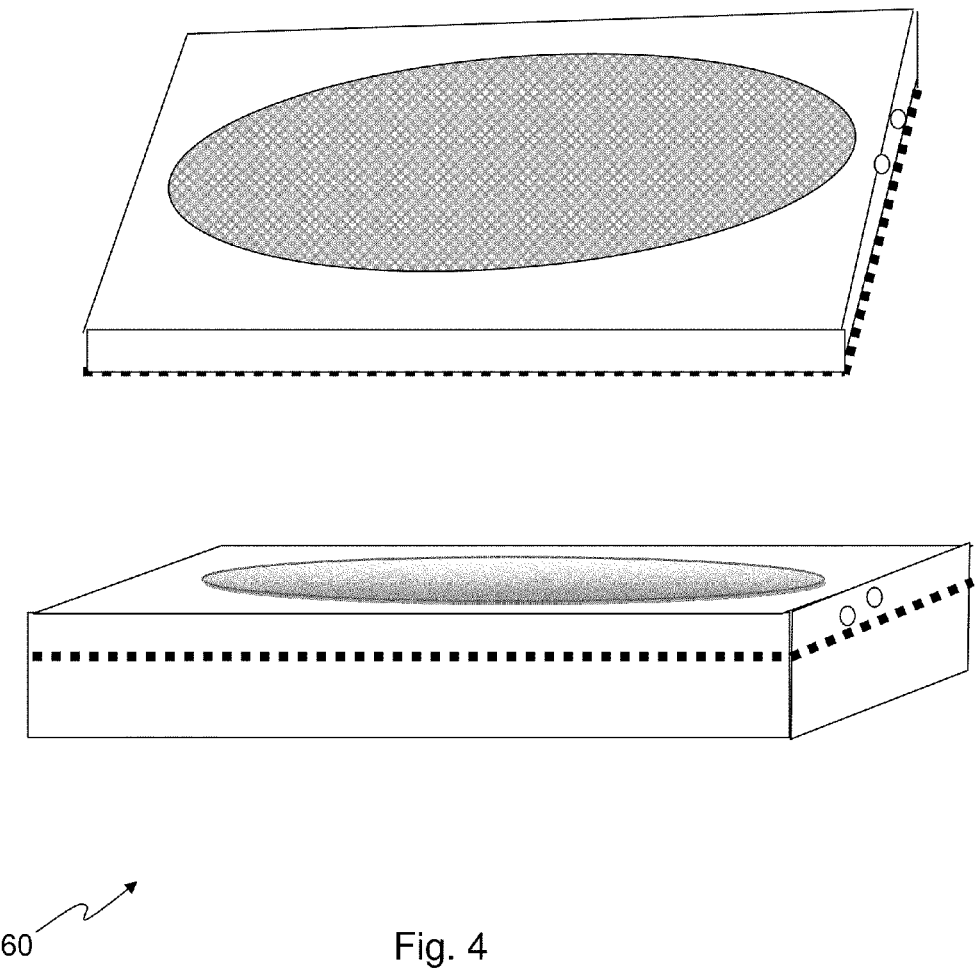
FIG. 4 is an exploded view of yet another embodiment mattress system.

FIG. 4 is an exploded perspective view of another embodiment mattress system 60 that is similar to the embodiment 50. However, whereas the embodiment system 50 has a core mattress that has a sloped top surface, the core mattress of the system 60 has a top surface that is substantially parallel to the bottom surface.

Figure 5:
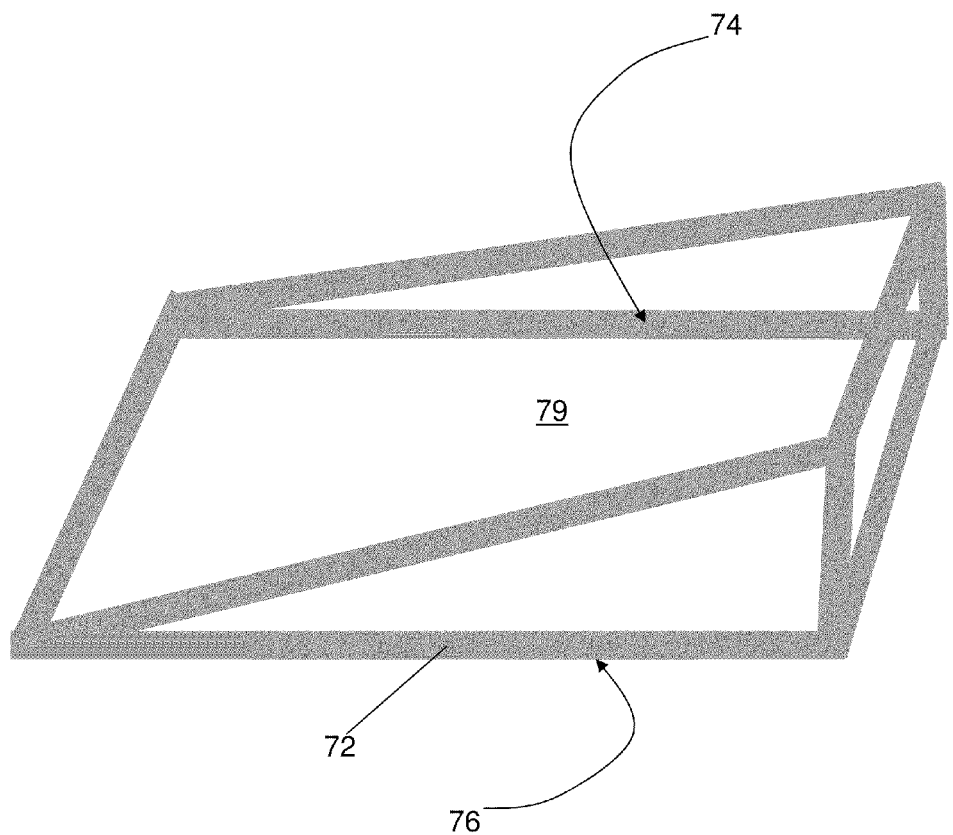
FIG. 5 is a perspective view of a first embodiment frame structure.

In various embodiment mattress systems the core mattress may be provided by a frame structure, and a corresponding mattress cover for the frame structure may be provided. For example, as shown in FIG. 5, an embodiment frame structure 70 comprises a series of supports 72, which may be made from any suitably rigid material, such as plastic, wood, metal or the like, and which may be covered with padding, such as cotton, wool, foam, rubber or the like to provide a resilient surface. The frame 70 may have a triangular shape to provide a sloping top surface 74 with respect to a bottom surface 76. A suitably shaped embodiment mattress cover may be provided to completely enclose the frame, in which the central region of the frame 70 serves as the depression 79 above which the hammock of the cover is suspended by way of the supports 72.

Figure 6:
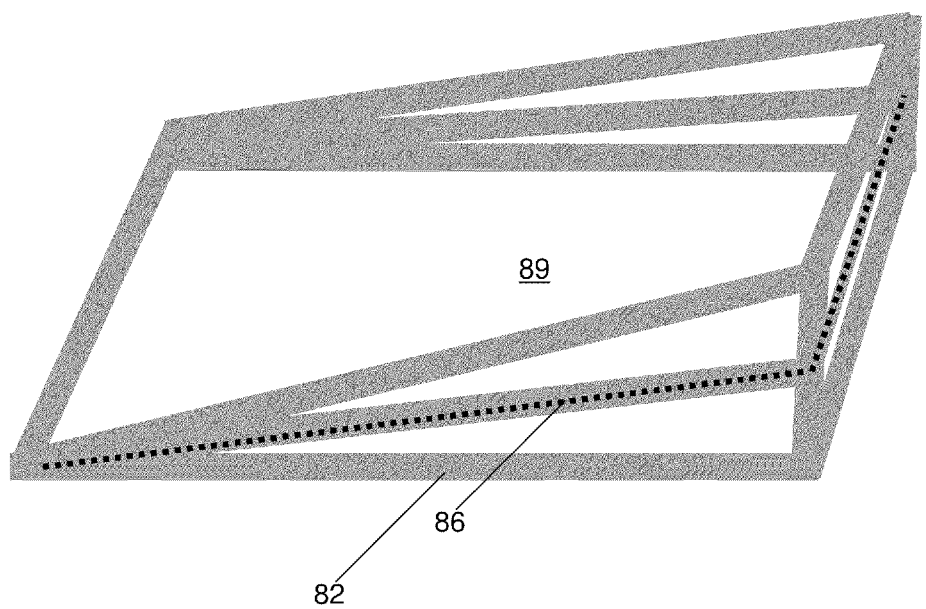
FIG. 6 is a perspective view of a second embodiment frame structure.

Another embodiment frame 80 is depicted in FIG. 6, which is adapted for embodiment mattress covers that do not fully enclose the 80. The frame system 80 is similar to the embodiment of FIG. 5, and includes padded supports 82 in a triangular formation. However, an anchoring system 86 is provided along one of the supports 82 that is used to removably couple to a corresponding anchoring system on the embodiment mattress cover, as discussed above in earlier embodiments. The anchoring system 86 preferably runs around the entire periphery of the frame 80. Hence, when the mattress cover is suspended over the depression 89, the anchoring system 86 accepts the load of the mattress cover.

Figure 7:
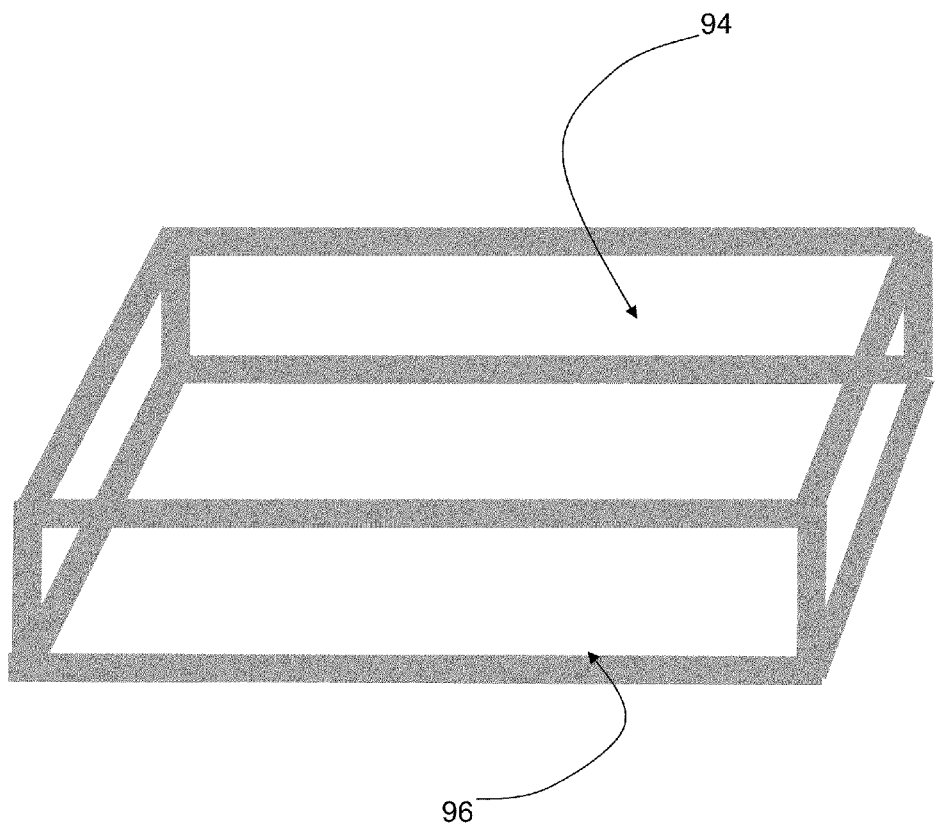
FIG. 7 is a perspective view of a third embodiment frame structure.
Figure 8:
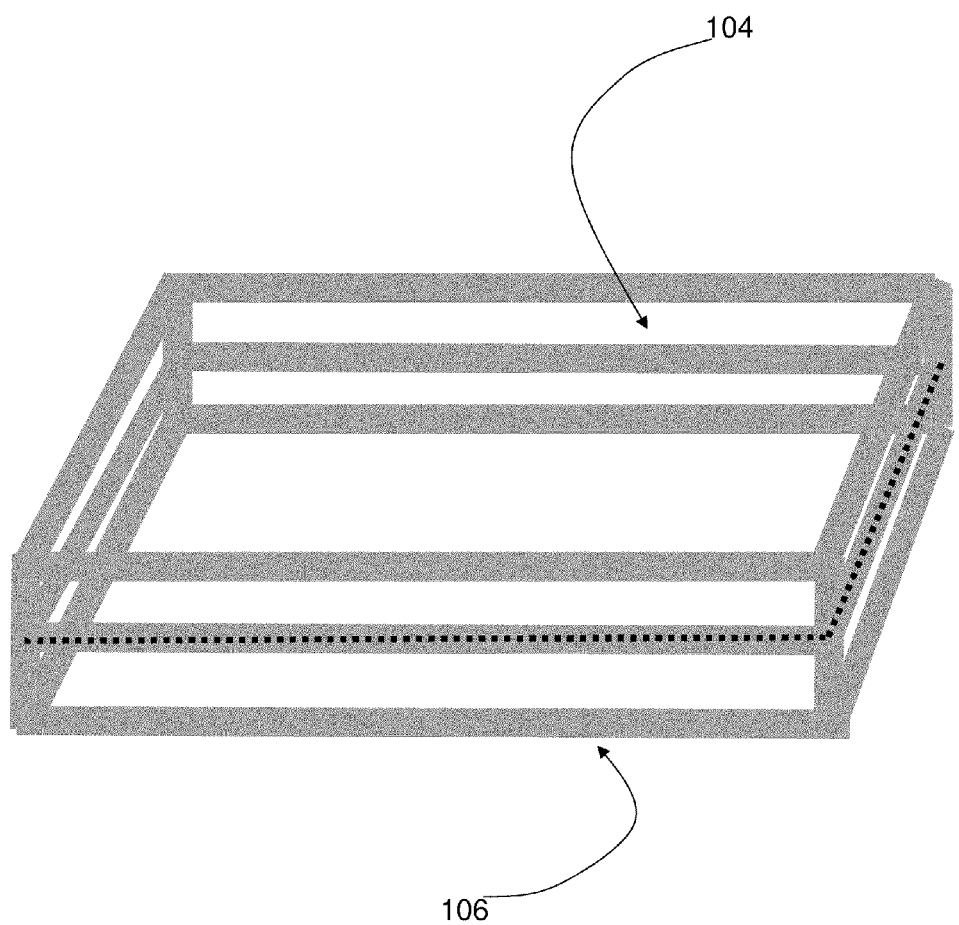
FIG. 8 is a perspective view of a fourth another embodiment frame structure.

An embodiment frame system 90 shown in FIG. 7 is substantially the same as that shown in FIG. 5, but the top surface 94 is substantially parallel to the bottom surface 96. Similarly, an embodiment frame system 100 shown in FIG. 8 is substantially the same as that shown in FIG. 6, but the top surface 104 is substantially parallel to the bottom surface 106.

Figure 9:
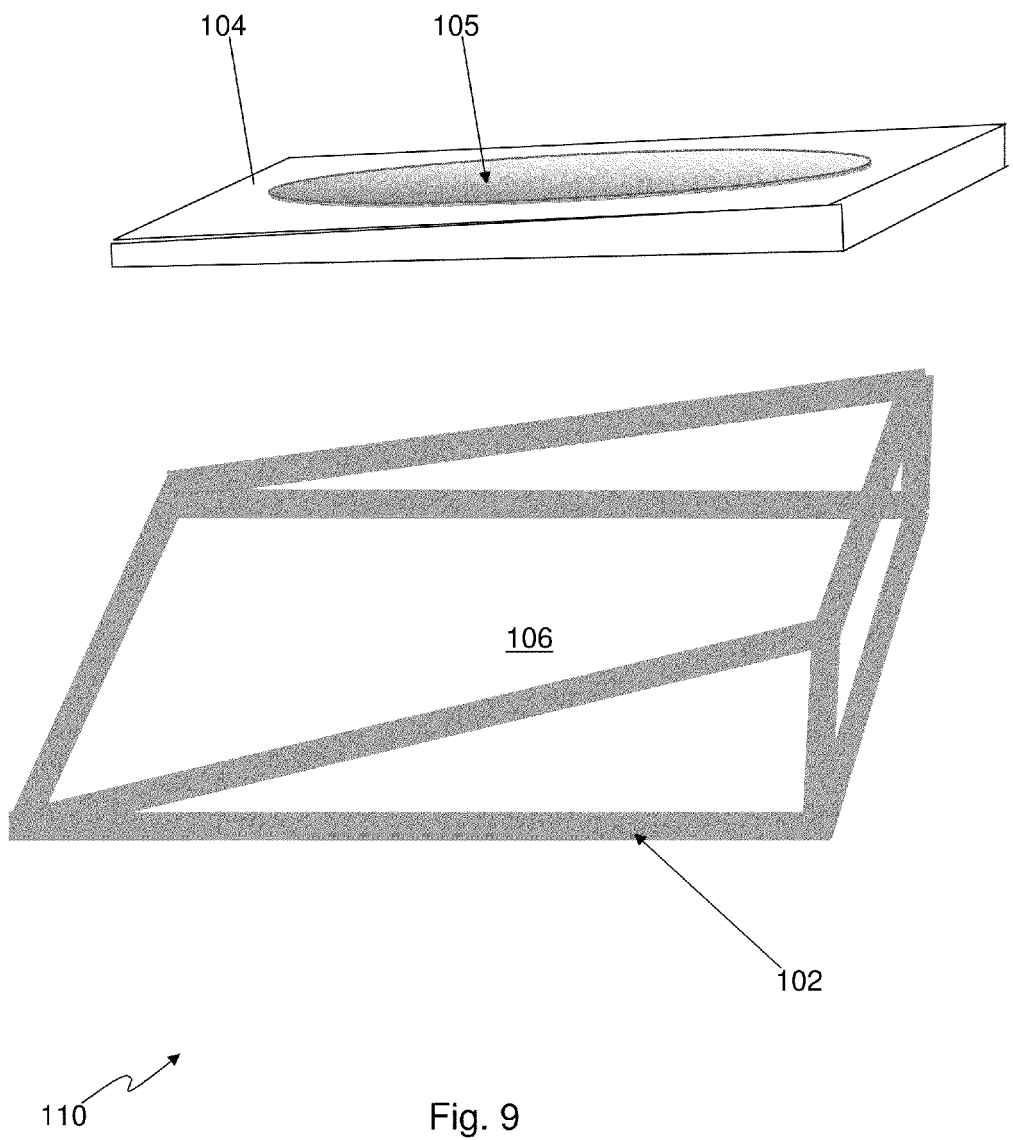
FIG. 9 is an exploded view of an embodiment core mattress.

In some embodiments the core mattress may include a frame structure as discussed above in combination with a relatively thin mattress pad that couples to the top surface defined by the frame structure. For example, as shown in FIG. 9, a frame structure 102, such as that disclosed in FIG. 5, is used to support a thin mattress pad 104. The mattress pad (made of polyurethane foam or coco fibers, for example) 104 includes a hole 105 that, in conjunction with the open area 106 provided by the frame 102, provides the depression for an embodiment mattress cover. The mattress pad 104 may be attached to the frame 102 by way of a complementary shape or by way of glue, laces, hook and loop fastener, buttons or any other suitable anchoring system. In some embodiments the mattress pad 104 and the frame 102 may be enclosed in mattress ticking. An embodiment mattress cover may then completely enclose the core mattress 110 provided by the frame 102 and pad 104 to provide an embodiment mattress system.

Figure 10:
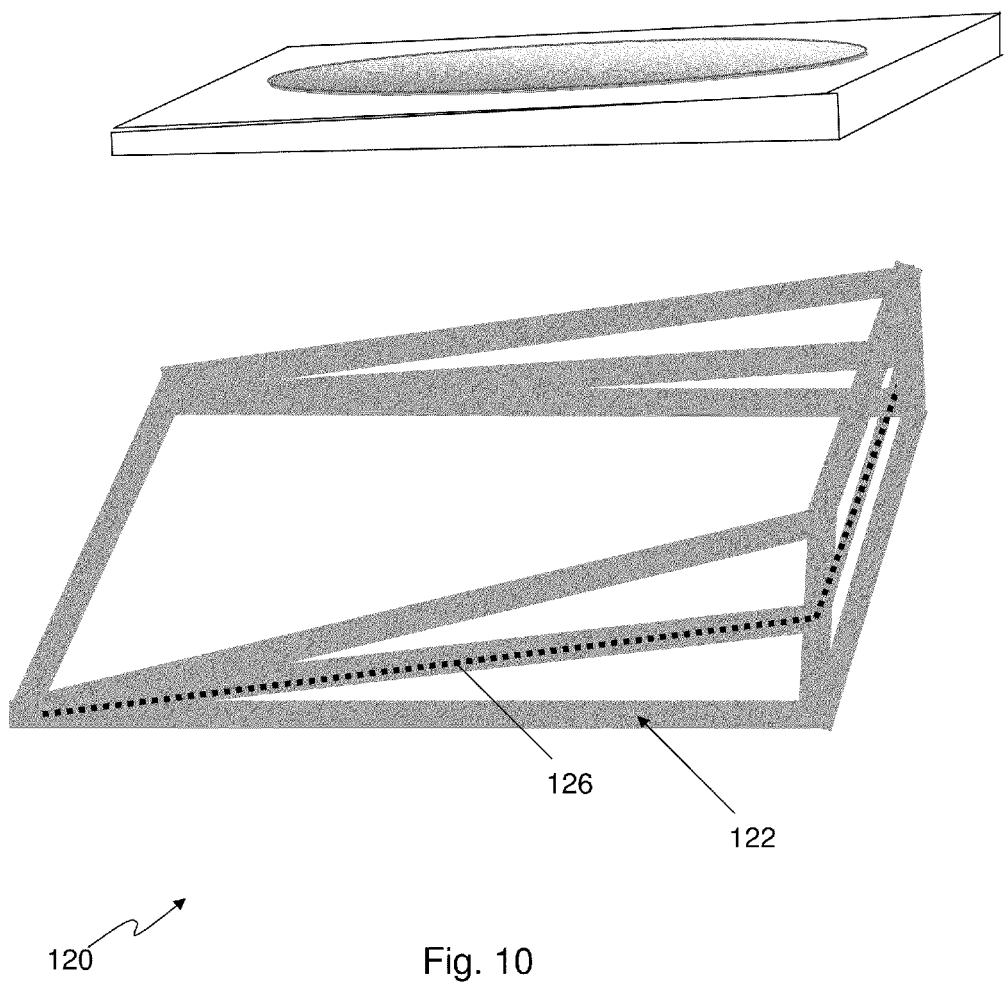
FIG. 10 is an exploded view of another embodiment core mattress.

The embodiment mattress core 120 shown in FIG. 10 is substantially the same as that discussed above with reference to FIG. 9, but instead uses a frame 122 similar to that shown in FIG. 6. In this case, rather than using an embodiment mattress cover that completely encloses the core mattress 120, a mattress cover analogous to that used with reference to FIG. 6 may be employed. Specifically, the core mattress 120 includes an anchoring system 126 that couples to a corresponding anchoring system on the mattress cover to removable fix the mattress cover to the frame 122. The embodiment mattress cover for the core mattress 86 may thus cover only the top surface of the core mattress and a portion of the sidewalls.

Figure 11:
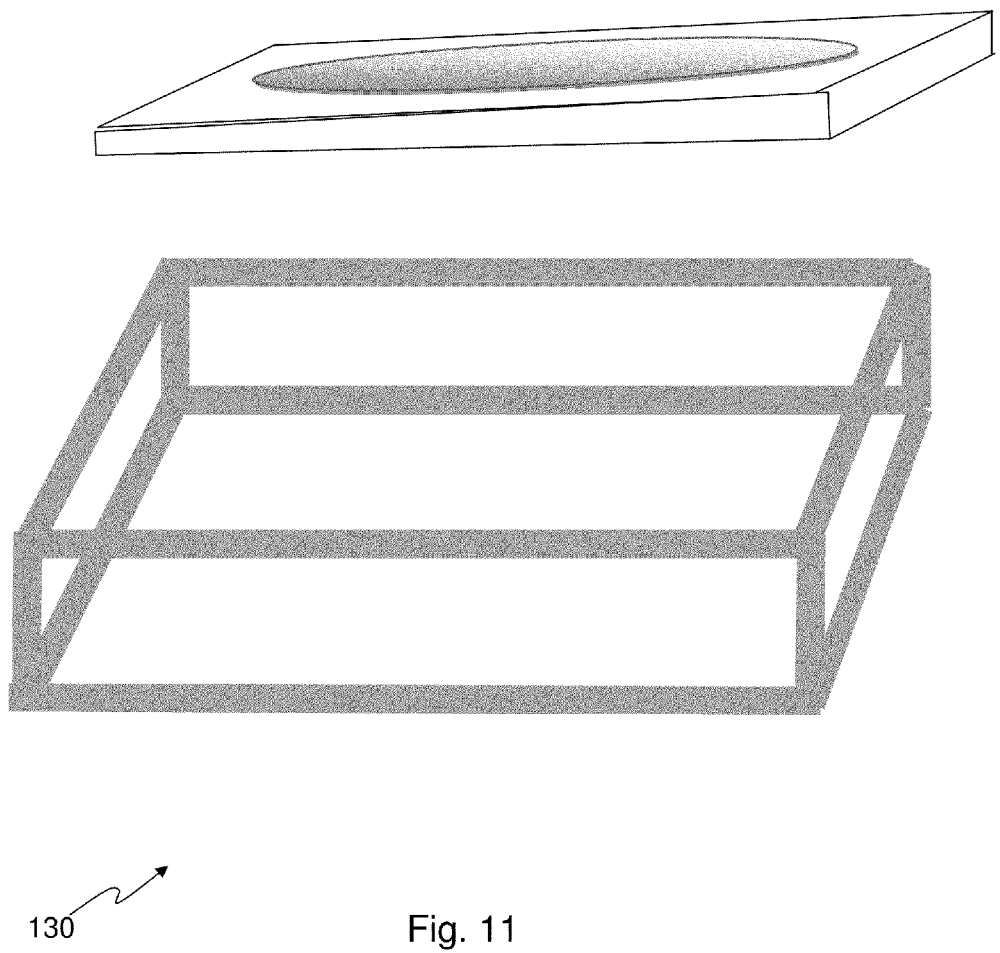
FIG. 11 is an exploded view of an yet another embodiment core mattress.
Figure 12:
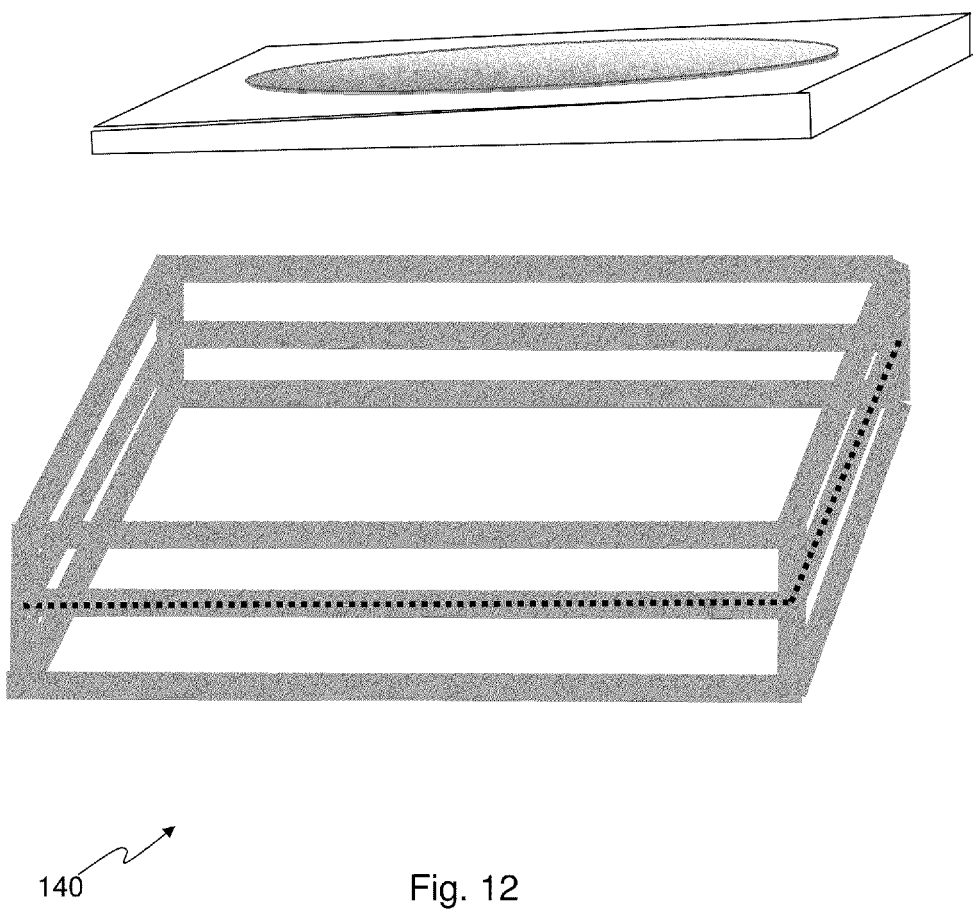
FIG. 12 is an exploded view of a further embodiment core mattress.

An embodiment core mattress 130 shown in FIG. 11 is substantially the same as that depicted in FIG. 9, but instead has a top surface that is parallel to the bottom surface of the core mattress, rather than being sloped as in FIG. 9. Similarly, the core mattress 140 shown in FIG. 12 is substantially similar to that shown in FIG. 10 but, again, has substantially parallel top and bottom surfaces.

Figure 13:
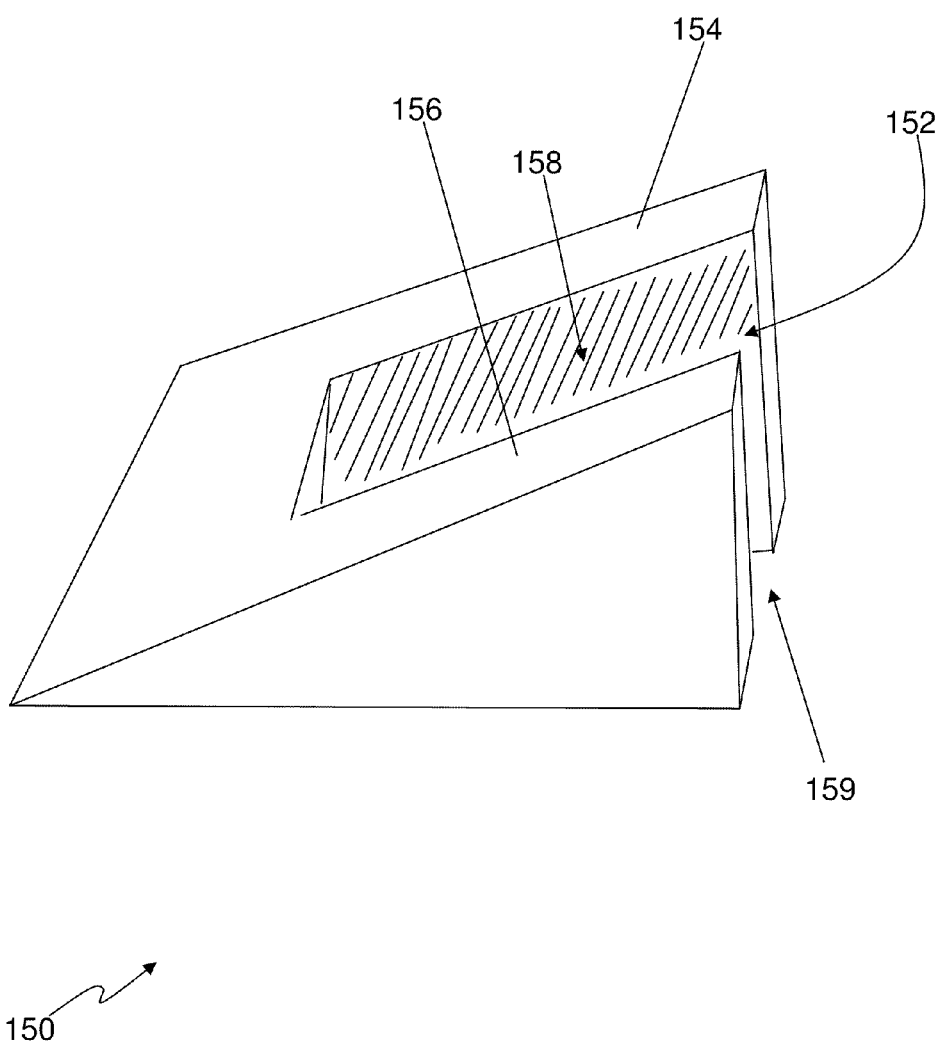
FIG. 13 is a perspective view of an embodiment core mattress in which a depression in the core mattress is missing a sidewall.

FIG. 13 illustrates another method employed by a core mattress to provide the depression. The core mattress 150 includes a U-shaped cut-out region 152 that provides the depression 158, and that effectively forms two wings 154, 156 on the core mattress 150 that extend towards the posterior end of the core mattress 150 and between which the hammock is suspended by way of an embodiment mattress cover. The U-shaped cut-out region 152 ensures a maximal amount of recirculation within the depression 158. As such, an embodiment mattress cover may include a mesh-like or other breathable fabric that wholly or partially covers the posterior end 159 of the U-shaped cut-out 152. A stiffening system may be employed within the core mattress 150 to reinforce the wings 154, 156, such as by way of a U-shaped support that runs along the sidewalls of the depression 158, rods that extend through the wings 154, 156, etc.

Figure 14:
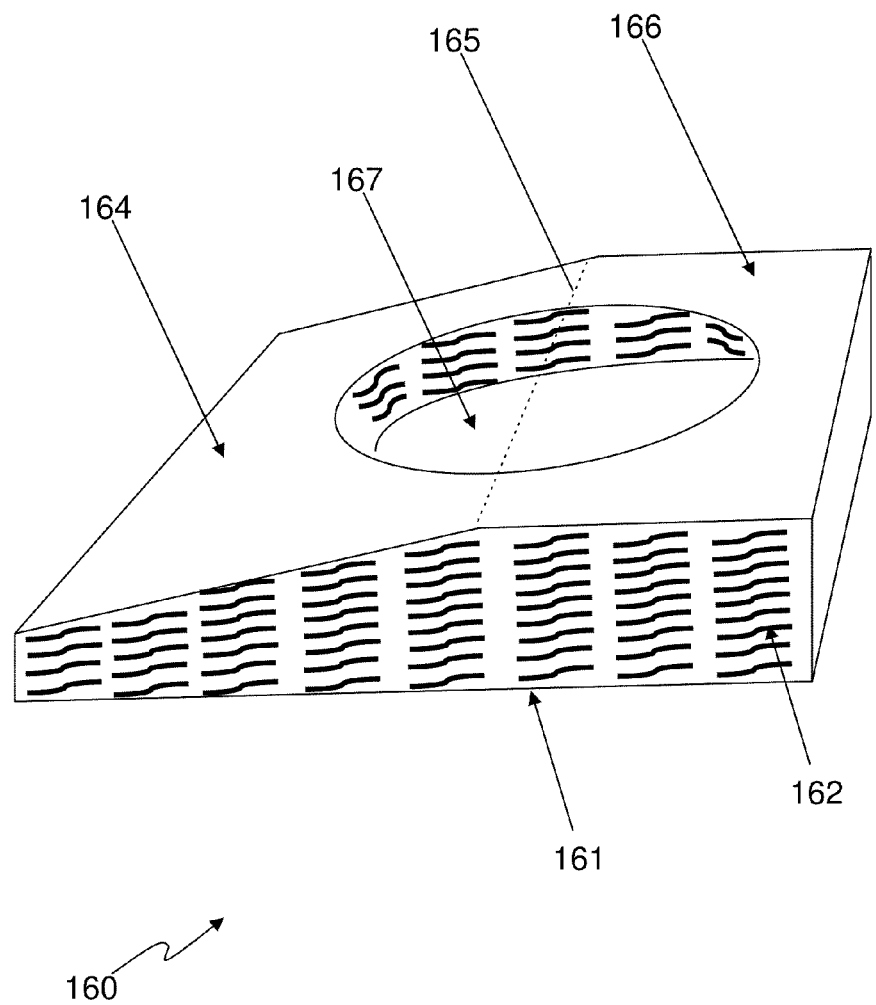
FIG. 14 is a perspective view of another embodiment core mattress that employs springs.

In some embodiment core mattress, as shown in FIG. 14, rather than using foam or ticking as disclosed above, springs 162 may be employed, as conventionally known, to provide the desired resiliency of the core mattress 160. Additionally, as shown in FIG. 14, the entire top surface of a core mattress need not all be at the same angle of inclination. For example, the anterior end 164 may be sloped, as disclosed in the above embodiments, but the posterior end 166 may be flat (i.e., parallel to the bottom surface 161). The transition line 165 between the sloped top surface 164 and the flat top surface 166 may be, for example, along the midline of the depression 167. However, other locations of the transition line 165 are certainly possible. It will be appreciated that this type of multi-angled sloping of the top surface of the core mattress may be employed with any of the above embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A mattress system adapted for the entire body of a subject to sleep on comprising:
    a core mattress adapted for the entire body of a subject to sleep on comprising a resilient material, the core mattress defining a top surface with a depression;
    a fabric mattress cover removably disposed around the core mattress and adapted to fully encompass the depression, the mattress cover comprising a breathable material disposed over a bottom surface of the depression, the breathable material forming a hammock suspended over the bottom surface and onto which the subject may be at least partially disposed and thereby suspended over the bottom surface; and
    a mesh coupled to the core mattress and disposed over the depression to provide additional support for the breathable material.

2. The mattress system of claim 1 further comprising a stiffening system to impart rigidity to the core mattress to substantially reduce bending of the core mattress under the weight of the child.

3. The mattress system of claim 1 wherein the mattress has an opening in a sidewall thereof for providing air, oxygen, or aerosols to the depression, and a connector for removably coupling the opening to a supply tube.

4. The mattress system of claim 3 wherein the mattress cover further comprises an opening or breathable fabric in register with the opening in the sidewall of the core mattress.

5. The mattress system of claim 4 wherein the mattress cover further comprises a connector for removably coupling to a supply tube.

6. The mattress system of claim 1 further comprising a ventilator positioned to provide circulation of air within the depression.

7. The mattress system of claim 1 wherein the core mattress comprises an anchoring system to mechanically couple the core mattress to an external device.

8. The mattress system of claim 7 wherein the mattress cover comprises one or more openings in register with the anchoring system of the core mattress.

9. The mattress system of claim 1 wherein the mattress cover further comprises an anchoring system to mechanically couple the core mattress to an external device.

10. The mattress system of claim 1 wherein the mattress cover further comprises a first coupling mechanism, the core mattress further comprises a second coupling mechanism, and the first and second coupling mechanisms are adapted to releasably connect with each other to removably dispose the mattress cover over the depression of the core mattress.

11. The mattress system of claim 1 wherein the mattress cover is bag-shaped and conformal to the shape of the core mattress to fully enclose the core mattress.

12. The mattress system of claim 1 wherein the breathable material is a mesh.

13. The mattress system of claim 1 wherein the mattress cover is made entirely of mesh material.

14. A mattress system adapted for the entire body of a subject to sleep on comprising:
- a core mattress adapted for the entire body of a subject to sleep on comprising a resilient material, the core mattress defining a top surface with a depression; and
- a fabric mattress cover removably disposed around the core mattress and adapted to fully encompass the depression, the mattress cover comprising a breathable material disposed over a bottom surface of the depression, the breathable material forming a hammock suspended over the bottom surface and onto which the subject may be at least partially disposed and thereby suspended over the bottom surface;
- wherein a sidewall of the depression is missing.

15. The mattress system of claim 14 further comprising a stiffening system to impart rigidity to the core mattress to substantially reduce bending of the core mattress under the weight of the child.

16. The mattress system of claim 14 wherein the mattress cover further comprises an opening or breathable fabric in register with an opening in the core mattress defined by the missing sidewall.

17. The mattress system of claim 14 further comprising a connector for removably connecting the opening in the core mattress to a supply tube.

18. The mattress system of claim 14 wherein said breathable material is a mesh.

19. A mattress system for an entire child to sleep on comprising:
- a core mattress for a child to sleep on comprising a resilient material, the core mattress being large enough for an entire child to sleep upon and defining a top surface with a depression therein, the depression comprising at least one of an indentation in the top surface of the core mattress, a hole passing all the way through the core mattress, a cutout section of the core mattress, and a cutout region of the core mattress;
- wherein a sidewall of the core mattress has an opening therein in fluid communication with the depression for allowing air to pass therebetween; and
- a mattress cover removably disposed around the core mattress and adapted to fully encompass the depression, the mattress cover comprising a breathable material disposed over the depression, wherein a child placed on the breathable material is held in a hammock that is suspended over a lowermost extent of the depression, the child being at least partially disposed within the depression;
- wherein:
- the mattress cover is configured to allow passage of air through the opening; and
- the hammock comprises a mesh material that is coupled to the core mattress, the breathable material of the mattress cover being disposed over the mesh material.

20. The mattress system of claim 9 further comprising a stiffening system to impart rigidity to the core mattress to substantially reduce bending of the core mattress under the weight of the child.

* * * * *

UNITED STATES PATENT AND TRADEMARK OFFICE
CERTIFICATE OF CORRECTION

| | |
|---|---|
| PATENT NO. | : 8,745,793 B2 |
| APPLICATION NO. | : 12/790538 |
| DATED | : June 10, 2014 |
| INVENTOR(S) | : Jose Bensoussan |

It is certified that error appears in the above-identified patent and that said Letters Patent is hereby corrected as shown below:

In the Claims

In claim 20, column 14, line 28, delete "9" and insert --19--.

Signed and Sealed this
Twelfth Day of August, 2014

Michelle K. Lee
*Deputy Director of the United States Patent and Trademark Office*